United States Patent
Sieg et al.

(10) Patent No.: US 8,937,718 B2
(45) Date of Patent: Jan. 20, 2015

(54) DEVICE AND METHOD FOR CALIBRATING A SCATTERED LIGHT METER

(75) Inventors: Raymond Sieg, Esslingen (DE); Karl Stengel, Deizisau (DE); Gerhard Haaga, Ohmden (DE); Michael Neuendorf, Plochingen (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 13/581,271

(22) PCT Filed: Jan. 3, 2011

(86) PCT No.: PCT/EP2011/050032
§ 371 (c)(1),
(2), (4) Date: Nov. 19, 2012

(87) PCT Pub. No.: WO2011/104040
PCT Pub. Date: Sep. 1, 2011

(65) Prior Publication Data
US 2013/0057860 A1    Mar. 7, 2013

(30) Foreign Application Priority Data
Feb. 26, 2010  (DE) .......................... 10 2010 002 423

(51) Int. Cl.
*G01N 21/00* (2006.01)
*G01N 21/47* (2006.01)
*G01N 21/53* (2006.01)

(52) U.S. Cl.
CPC ............ *G01N 21/4785* (2013.01); *G01N 21/53* (2013.01)

USPC .......................................... 356/341; 356/337

(58) Field of Classification Search
USPC ................... 356/335–343, 243.1, 243.8, 319
See application file for complete search history.

(56) References Cited

U.S. PATENT DOCUMENTS

| | | | |
|---|---|---|---|
| 3,234,846 A | 2/1966 | Cropper et al. | |
| 4,291,981 A | 9/1981 | Ohnishi et al. | |
| 5,059,811 A | 10/1991 | King et al. | |
| 5,999,257 A | 12/1999 | Myers et al. | |
| 2004/0008343 A1* | 1/2004 | Pawluczyk et al. | 356/243.1 |
| 2004/0202578 A1* | 10/2004 | Burtscher et al. | 422/83 |

FOREIGN PATENT DOCUMENTS

JP  10239237  9/1998

OTHER PUBLICATIONS

International Search Report, PCT International Application No. PCT/EP2011/050032, dated May 19, 2011.
Karabegov, M. et al., "Liquid and Solid-State Samples for Calibrating Turbidimeters and Nephelometers," *Measurement Techniques*, vol. 40, No. 12, pp. 1216-1220, 1997.

* cited by examiner

*Primary Examiner* — Tri T Ton
(74) *Attorney, Agent, or Firm* — Kenyon & Kenyon LLP

(57) ABSTRACT

A calibration apparatus for calibrating a scattered-light measuring device that is embodied to measure a particle concentration in motor vehicle exhaust gases, comprises at least one scattering body that has a number of scattering centers having a defined size and a defined mutual spacing. The scattering centers are disposed in such a way that the scattering body, upon irradiation with light from a light source, delivers scattered light having an intensity and a distribution predetermined by the scattering body.

9 Claims, 3 Drawing Sheets

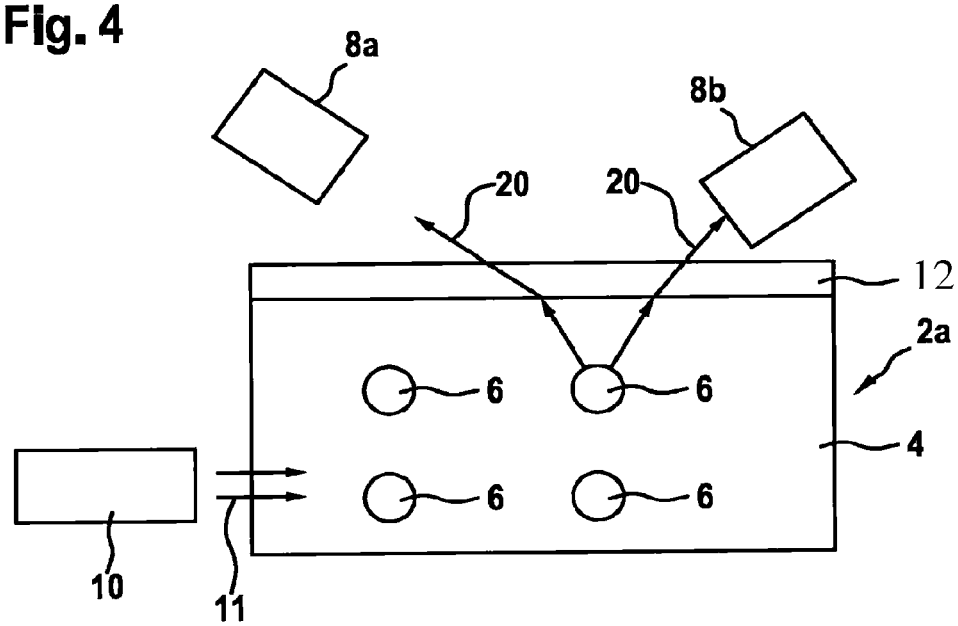
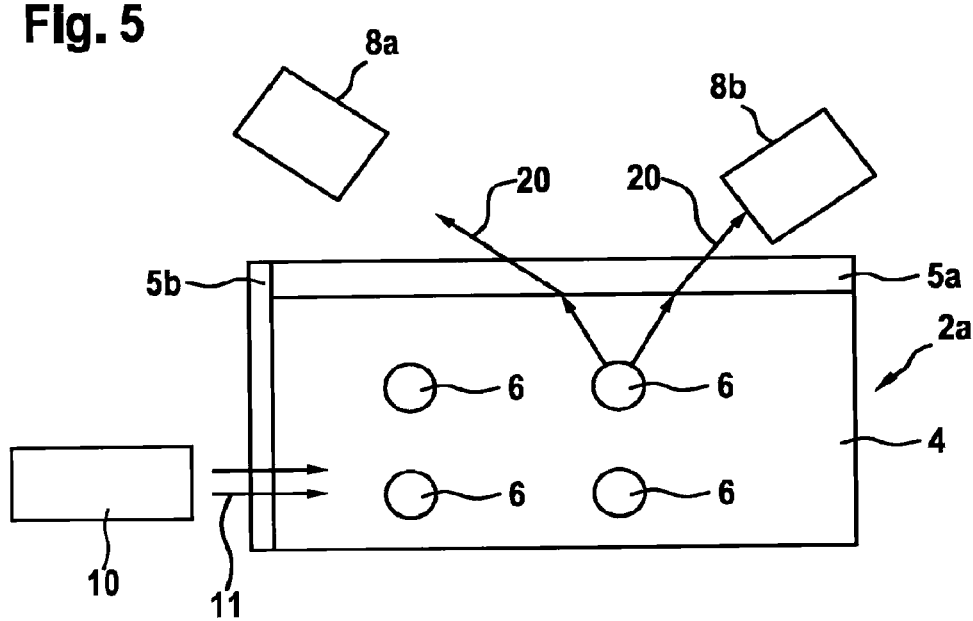

DEVICE AND METHOD FOR CALIBRATING A SCATTERED LIGHT METER

FIELD OF THE INVENTION

The present invention relates to an apparatus and a method for calibrating a scattered-light measuring device that is used for measuring particle concentrations in motor vehicle exhaust gases.

BACKGROUND INFORMATION

Conventionally, scattered-light methods are used to measure the concentration of particles in exhaust gases and other colloids.

It is usual to use in this context a high-intensity light source, for example a laser, that radiates light into a measurement chamber through which the colloid to be measured is being guided. At least one light sensor, which detects light that has been scattered from particles present in the colloid, is present. In order to check for proper functionality of a scattered-light measuring device of this kind, and to calibrate the device, it is necessary to establish in the measurement chamber a defined state in which the irradiated light is scattered in a defined and known manner. Scattered-light measuring devices that are used for official measurements are subject to a calibration requirement, further increasing the need to supply accurate and highly reliable measurement results.

SUMMARY

It is an object of the present invention to make available an apparatus that enables simple, reliable, and accurate checking and calibration of a scattered-light measuring.

An example calibration apparatus according to the present invention for calibrating a scattered-light measuring device that is embodied to measure a particle concentration in motor vehicle exhaust gases has at least one scattering body. In the scattering body are a number of scattering centers which are disposed in such a way that the scattering body, upon defined irradiation with light, delivers a scattered-light pattern having an intensity and a distribution predetermined by the scattering body.

With a scattering body that has a disposition of scattering centers that is defined in this manner, a defined scattered-light pattern can be generated easily and quickly in the measurement chamber. As compared with the use of a calibration gas or of conventional calibration apparatuses that, for example, have reflective planes, a scattering body of this kind is easier to handle and can more easily be manufactured with reproducible properties and the requisite accuracy. A scattering body of this kind is also not subject to either wear or abrasion during calibration.

The present invention also encompasses a scattered-light measuring device for measuring a particle concentration in motor vehicle exhaust gases, having a scattered-light measurement chamber, at least one light source, and at least one scattered-light sensor, the measurement chamber having at least one receiving apparatus that is embodied for reception of a calibration apparatus according to the present invention. A scattered-light measuring device of this kind can be calibrated particularly well because the calibration apparatus is particularly easy to introduce into the measurement chamber.

The present invention also encompasses a method for calibrating a scattered-light measuring device for measuring the particle concentration in motor vehicle exhaust gases, having a scattered-light measurement chamber, at least one light source, and at least one scattered-light sensor, the method encompassing introducing a calibration apparatus according to the present invention into a defined position in the scattered-light measurement chamber, illuminating the calibration apparatus with light from the light source, receiving, with the light sensor, light scattered from the calibration apparatus (scattered light), and comparing the signal outputted from the light sensor with a predetermined reference value.

Such a method allows a scattered-light measuring device to be calibrated particularly simply and reliably, with high accuracy. In particular, it is possible to dispense with the use of special calibration gases, which are complicated to store and handle and in which the particle concentration is dependent on external parameters such as, for example, pressure and/or temperature.

In an example embodiment, the scattering body has a transparent carrier material in which the scattering centers are disposed in the transparent carrier material. In a transparent carrier material, the scattering centers can be disposed particularly effectively in a defined structure in order to generate a defined scattered-light pattern upon irradiation with light. The scattering centers can be embodied, for example, as crystals within the carrier material.

In an example embodiment, the scattering centers have a defined size and/or are disposed with defined mutual spacings within the scattering body. In an embodiment, the scattering centers are disposed within the scattering body in an ordered structure, for example in a regular lattice. A scattering body in which the scattering centers are disposed in an ordered structure has particularly well-defined scattering characteristics.

In an example embodiment, the carrier material contains a glass ceramic. Glass ceramic is a particularly suitable carrier material because it possesses high transparency, high strength, and low thermal expansion. When the carrier material is highly transparent, calibration can be carried out even at low light intensities. High strength and low thermal expansion allow any change in the intensity distribution of the scattered-light pattern as a result of external influences, in particular mechanical influences and/or temperature changes, to be avoided or at least reduced, so that the calibration can always be carried out with high accuracy regardless of external influences.

In an example embodiment, the scattering body has on at least one surface a toned layer or an additional gray glass filter. Thanks to a toned layer, or the gray glass filter, disposed on a surface, the intensity of the scattered light can be adjusted as required. The use of different scattering bodies having variously toned layers or gray glass filters allows the calibration to be carried out at different light intensities. As a result, the calibration can be carried out over a wide intensity range, so that the measuring instrument is operable with high accuracy over a wide intensity range.

In an example embodiment, the calibration apparatus has at least one mount for receiving the scattering body. A mount allows the scattering body to be attached in particularly simple, and optionally replaceable, fashion on the calibration apparatus.

In an example embodiment, the receiving apparatus is embodied so that the scattering body is disposed in a defined position within the measurement chamber when a calibration apparatus is received in the receiving apparatus. A receiving apparatus of this kind ensures that the calibration apparatus is located in a defined position within the measurement chamber during calibration, and that a defined scattered-light distribution is generated upon irradiation by a light source. The calibration can be performed simply and with high accuracy. The position of the calibration apparatus does not need to be laboriously adjusted before each calibration operation, and errors in calibration that can be caused by an incorrectly disposed scattering body are avoided.

In an example embodiment, the calibration apparatus is immobilizable in the receiving apparatus. Immobilization ensures that the calibration apparatus maintains its defined position during calibration, and delivers scattered light having a defined intensity distribution when irradiated. Incorrect calibration caused by an incorrectly placed calibration apparatus can thus be reliably avoided.

The present invention also encompasses the use of a scattering body that contains a number of scattering centers having a defined size and a defined mutual spacing, so that upon defined irradiation by a light source, the scattering body delivers scattered light having a predetermined intensity and distribution for calibration of a scattered-light measuring device that is embodied to measure a particle concentration in motor vehicle exhaust gases or other colloids.

BRIEF DESCRIPTION OF THE DRAWINGS

Exemplifying embodiments of the invention are described in further detail below with reference to the figures.

FIG. 4 schematically shows the construction and function of a scattering body in accordance with a second exemplifying embodiment.

FIG. 5 schematically shows the construction and function of a scattering body in accordance with a variant of the second exemplifying embodiment.

DETAILED DESCRIPTION OF EXAMPLE EMBODIMENTS

Figure 1:
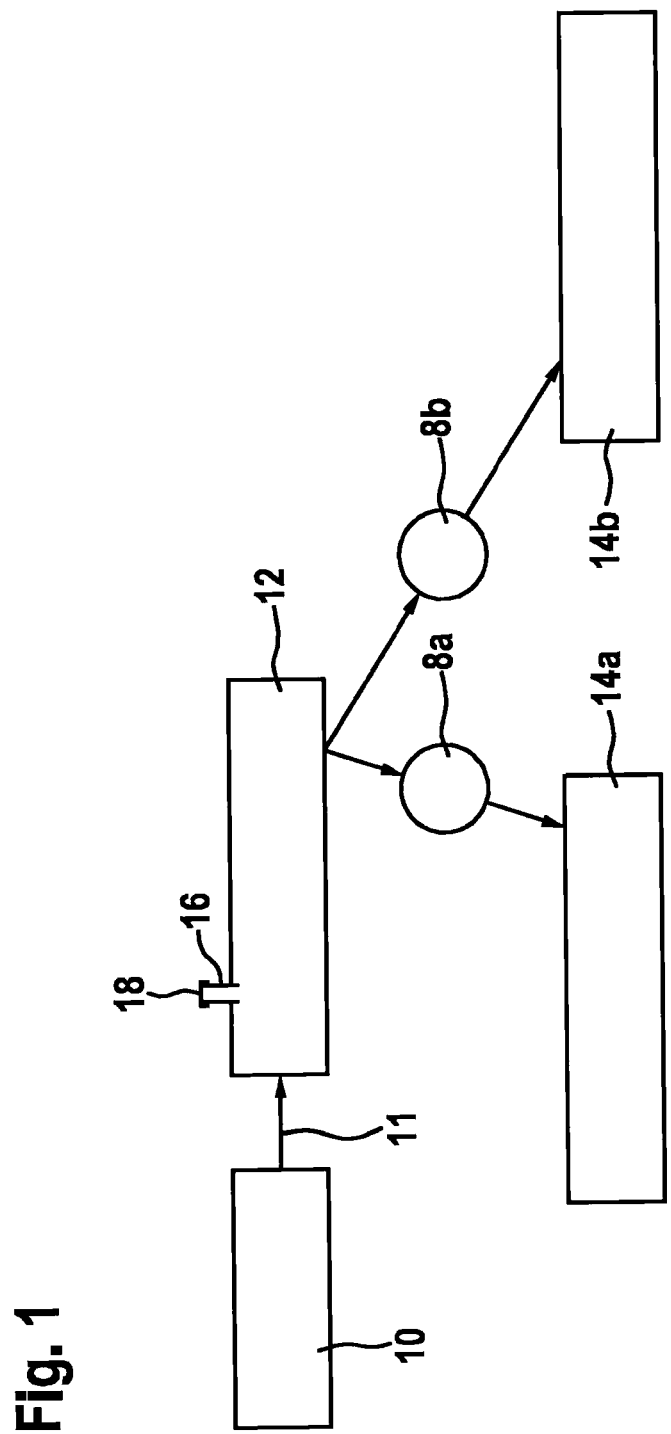
FIG. 1 schematically shows the construction of a scattered-light measuring device.

FIG. 1 schematically shows the construction of a scattered-light measuring device for measuring a particle concentration in motor vehicle exhaust gases or other colloids.

A scattered-light measuring device of this kind has a scattered-light measurement chamber 12 through which exhaust gas from a motor vehicle is guided via inlet and outlet conduits (not shown in FIG. 1). The exhaust gas can be guided through the measurement chamber by the pressure (so-called "exhaust gas back pressure") generated by the engine of the motor vehicle. Optionally, a pump (not shown in FIG. 1) can additionally be provided in order to assist the flow of exhaust gas through measurement chamber 12.

The scattered-light measuring device has at least one light source 10 that is embodied, for example, as a laser. Light source 10 generates, in the switched-on state, a light beam 11 having a defined intensity and direction within measurement chamber 12.

Also provided in measurement chamber 12 is/are at least one, in the exemplifying embodiment shown in FIG. 1 two, light sensors 8a, 8b that detect light from light source 10 that has been scattered from particles that are present in the exhaust gas stream passed through measurement chamber 12. In the schematic depiction of FIG. 1, light source 10 and light sensors 8a, 8b are depicted outside measurement chamber 12 for better clarity, although in reality they are disposed at least partly inside or directly on scattered-light measurement chamber 12.

Light sensors 8a, 8b are preferably disposed at different angles with reference to the direction of the irradiated light beam 11, so that they detect scattered light 20 scattered at different angles. The electrical signals output by scattered-light sensors 8a, 8b are conveyed to one or more electronic amplification and evaluation devices 14a, 14b that evaluate the signals and ascertain and output the concentration of particles in the gas stream passed through measurement chamber 12.

In order to obtain highly accurate measurement results, which for example meet stringent legal requirements, a scattered-light measuring device should be regularly calibrated. For this, scattered light that corresponds to a predetermined known particle concentration is generated in measurement chamber 12, and evaluation devices 14a, 14b are adjusted so that they output the predetermined known particle concentration as a result of the measurement.

According to the present invention, measurement chamber 12 has at least one receiving apparatus 16 for receiving a calibration apparatus according to the present invention. In the exemplifying embodiment shown, receiving apparatus 16 is embodied as an opening through which a calibration apparatus according to the present invention, as described hereinafter, can be introduced into measurement chamber 12.

If a calibration apparatus is not introduced into measurement chamber 12, the opening of receiving apparatus 16 is closed off by a cover 18 in order to prevent the penetration of particles and/or light from the environment into measurement chamber 12, and a distortion of measurement results caused thereby.

In an alternative exemplifying embodiment that is not shown, calibration apparatus 1 can be introduced into measurement chamber 12 through one of the openings (not shown in FIG. 1) that are provided for the introduction or discharge of the motor vehicle exhaust gases. This is possible because no exhaust gases are passed through measurement chamber 12 during the calibration operation.

Figure 2:
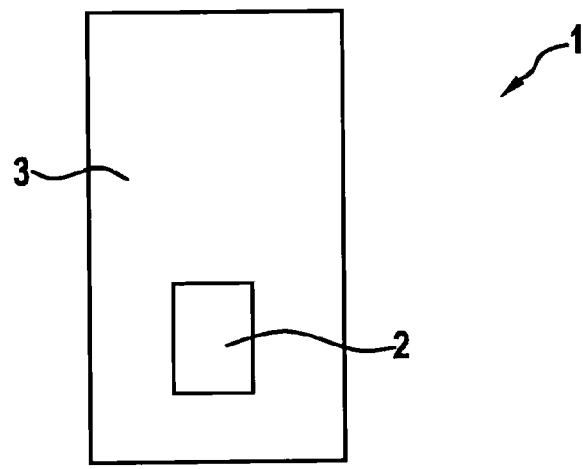
FIG. 2 schematically shows the construction of a calibration apparatus according to the present invention.

FIG. 2 is a schematic depiction showing the construction of a calibration apparatus 1 according to the present invention.

A calibration apparatus 1 according to the present invention has a holder 3, which is embodied for example as a cylindrical peg or (sheet-metal) strip and on which a scattering body 2 according to the present invention is attached.

Scattering body 2 can, for example, be adhesively bonded onto holder 3 so that the position of scattering body 2 on holder 3 is fixed. This ensures that scattering body 2 is always in the desired defined position during calibration.

Alternatively, a mount (not shown in FIG. 2), which receives and secures scattering body 2 in a defined position, can be provided on holder 3. The mount can be configured in such a way that scattering body 2 is replaceable. A single holder 3 can thus be used with a variety of scattering bodies 2.

Calibration apparatus 1 is embodied in such a way that it can be introduced into the opening, embodied in measurement chamber 12, of receiving apparatus 16 and can be immobilized there. When calibration apparatus 1 is introduced into measurement chamber 12 and immobilized there, measurement element 2 has a defined position within measurement chamber 12 and, upon irradiation with light 11 from light source 10, generates a defined scattered-light pattern.

A seal (not shown in FIG. 2) can be provided on holder 3 in order to seal off the opening of receiving apparatus 16 in light-tight fashion when calibration apparatus 1 is disposed in receiving apparatus 16. This prevents the calibration from being distorted by ambient light that penetrates through opening 16 into measurement chamber 12.

Figure 3:
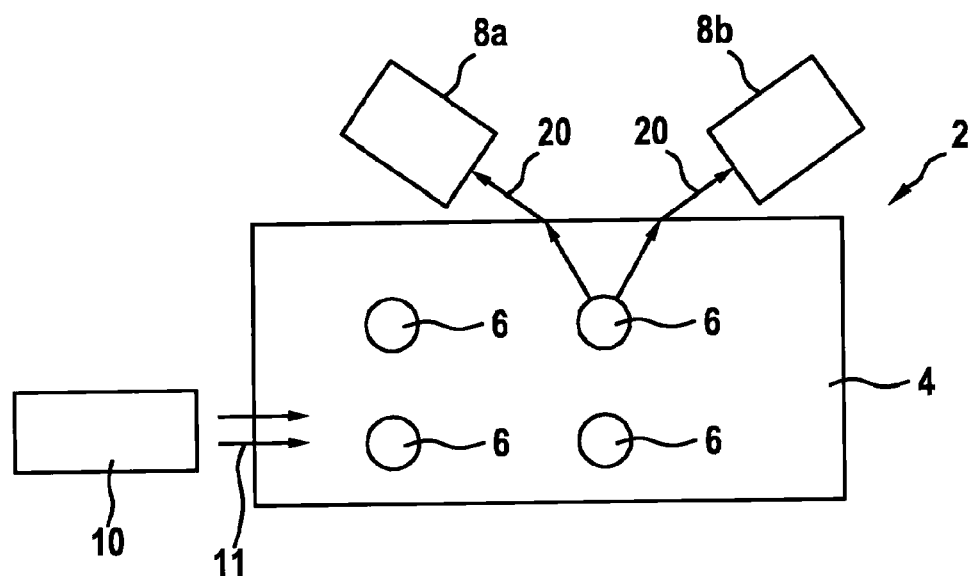
FIG. 3 schematically shows the construction and function of a scattering body in accordance with a first exemplifying embodiment.

FIG. 3 schematically depicts a scattering body 2 in accordance with a first exemplifying embodiment, as used in a calibration apparatus 1 according to the present invention.

A scattering body 2 according to the present invention has a transparent carrier material 4 that is preferably a material having a particularly low thermal expansion, for example a glass ceramic material. A number of scattering centers 6 are disposed in carrier material 4, scattering centers 6 having a defined size and a defined mutual spacing. Scattering centers 6 are preferably disposed within carrier material 4 in a regular lattice structure, as shown schematically in FIG. 3. Scattering centers 6 can be crystals embodied in the carrier material.

A scattering body 2 constructed in this fashion has defined scattering properties that are constant over a long period of time, so that upon irradiation with light 11 from light source 10, it delivers scattered light 20 having an intensity and a spatial distribution defined by scattering body 2. Scattered light 20 generated by scattering body 2 strikes scattered-light sensors 8a and 8b and is detected by them, as shown schematically in FIG. 3.

In order to carry out a calibration according to the present invention, a calibration apparatus 1 according to the present invention that has a scattering body 2 as shown in FIG. 3 is brought through the opening of receiving apparatus 16 into a defined position within measurement chamber 12. Light 11 generated by light source 10 is scattered by scattering body 2 in a defined, predetermined spatial intensity distribution, and the light that is scattered (scattered light) 20 is acquired by scattered-light sensors 8a, 8b and converted into electrical signals. The electrical signals are converted by one or more evaluation devices 14a, 14b into a particle concentration.

The particle concentration ascertained by evaluation devices 14a, 14b is compared with a defined particle concentration that is associated with the respective scattering body 2. If the particle concentration ascertained by evaluation devices 14a, 14b deviates from the predetermined particle concentration associated with scattering body 2, evaluation devices 14a, 14b are then readjusted until the particle concentration ascertained by evaluation devices 14a, 14b corresponds, within the predetermined accuracy, to the predetermined particle concentration associated with scattering body 2.

Comparison of the calculated particle concentration with the predetermined particle concentration, and the adjustment of evaluation devices 14a, 14b, can occur automatically or manually.

The use of a variety of scattering bodies 2, whose scattering behavior corresponds to the scattering behavior of exhaust gases having different particle concentrations, makes it easy to carry out calibration of the scattered-light measuring device at different operating points. Particularly accurate calibration of the scattered-light measuring device over a wide measurement range can thereby be achieved.

Advantageously, carrier material 4 of scattering body 2 has a particularly low thermal expansion, so that the scattering behavior of scattering body 2 is independent of ambient temperature over a wide temperature range. Unlike when a reference gas is used, calibration can then be carried out with high accuracy independently of ambient temperature.

FIG. 4 shows an alternative exemplifying embodiment of a scattering body 2a according to the present invention.

In this exemplifying embodiment as well, scattering body 2a has a carrier material 4 into which a number of scattering centers 6 are embedded. The construction of scattering body 2a corresponds in this regard to the construction of the first exemplifying embodiment as shown in FIG. 2.

In addition, scattering body 2a in accordance with the second exemplifying embodiment has at least one toned layer 12 or an additional gray glass filter 12, which is applied onto at least one surface of scattering body 2a and which attenuates or damps light that enters scattering body 2a, or emerges from it, through the coated surface of scattering body 2a or through the gray glass filter.

In the exemplifying embodiment shown in FIG. 4, toned layer 12 or through gray glass filter 12 is disposed in such a way that scattered light 20 which emerges from scattering body 2a is attenuated. Conversely, no toned layer 12 and no gray glass filter 12 are provided on that surface of scattering body 2a through which light beam 11 from light source 10 enters scattering body 2a.

In an alternative exemplifying embodiment shown in FIG. 5, toned layer 5b or gray glass filter 5b is also additionally embodied on that surface of scattering body 2a through which light beam 11 from light source 10 enters scattering body 2a. Alternatively, toned layer 5b or gray glass filter 5b can also be embodied exclusively on that surface of scattering body 2a through which light beam 11 from light source 10 enters scattering body 2a.

The application of at least one toned layer 5a, 5b or one gray glass filter 5a, 5b onto at least one surface of scattering body 2a allows the intensity of the light 11 from light source 10 entering scattering body 2a, and/or the intensity of scattered light 20 emerging from scattering body 2a, to be attenuated in controlled fashion.

If the intensity of light source 10 is too great, for example, overdriving of or damage to scattered light sensors 8a, 8b and/or evaluation devices 14a, 14b can be avoided by way of a toned layer 5a, 5b or gray glass filter 5a, 5b of this kind.

Different intensity levels of scattered light 20 can also be set in controlled fashion, so that the calibration can be carried out at different scattered-light intensities. In particular, scattering bodies 2a having layers 5a, 5b of different toning strengths or gray glass filters 5a, 5b of different toning strengths allow the setting of scattered-light intensities that differ in terms of percentage.

A calibration that is carried out at different scattered-light intensities allows the scattered-light measuring device to be calibrated over a wide intensity range, so that it furnishes measurement results with particularly high accuracy over a wide range of intensities.

What is claimed is:

1. A calibration apparatus for calibrating a scattered-light measuring device that measures a particle concentration in motor vehicle exhaust gases, the calibration apparatus comprising:
   at least one scattering body, wherein the scattering body includes a carrier material that has a number of scattering centers which are disposed in such a way that the scattering body, upon irradiation with light, delivers scattered light having an intensity and a distribution defined by the scattering body, wherein the scattering body includes one of at least one toned layer and a gray glass filter disposed on a surface of the scattering body, wherein the one of the at least one toned layer and the gray glass filter one of attenuates and dampens light that one of enters and exits through the one of the at least one toned layer and the gray glass filter.

2. The calibration apparatus as recited in claim 1, wherein the scattering centers have at least one of a defined size and a defined mutual spacing within the scattering body, and being disposed in an ordered structure within the scattering body.

3. The calibration apparatus as recited in claim 1, wherein the scattering body includes a transparent carrier material that contains a glass ceramic.

4. The calibration apparatus as recited in claim 1, wherein the scattering body includes at least one toned layer.

5. The calibration apparatus as recited in claim 1, wherein the calibration apparatus has at least one mount for reception of the scattering body.

6. A measuring device for measuring a particle concentration in motor vehicle exhaust gases, comprising:
   a scattered-light measurement chamber;
   at least one light source; and
   at least one scattered-light sensor;
   wherein the scattered-light measurement chamber has at least one receiving apparatus to receive a calibration apparatus including at least one scattering body, wherein the scattering body includes a carrier material that has a number of scattering centers which are disposed in such a way that the scattering body, upon irradiation with light from the light source, delivers scattered light having an intensity and a distribution defined by the scattering body, wherein the scattering body includes one of at least one toned layer and a gray glass filter disposed on a surface of the scattering body, wherein the one of the at least one toned layer and the gray glass filter one of attenuates and dampens light that one of enters and exits through the one of the at least one toned layer and the gray glass filter.

7. The measuring device as recited in claim 6, wherein the receiving apparatus is configured so that the scattering body is disposed in a defined position within the measurement chamber when the calibration apparatus is disposed in the receiving apparatus.

8. The measuring device as recited in claim 7, wherein the calibration apparatus is securable in the receiving apparatus.

9. A method for calibrating a scattered-light measuring device that measures the particle concentration in motor vehicle exhaust gases and includes a scattered-light measurement chamber, at least one light source, and at least one scattered-light sensor, the method comprising:
   introducing a calibration apparatus into the scattered-light measurement chamber, the calibration apparatus including at least one scattering body, wherein the scattering body includes a carrier material that has a number of scattering centers which are disposed in such a way that the scattering body, upon irradiation with light from the light source, delivers scattered light having an intensity and a distribution defined by the scattering body, wherein the scattering body includes one of at least one toned layer and a gray glass filter disposed on a surface of the scattering body, wherein the one of the at least one toned layer and the gray glass filter one of attenuates and dampens light that one of enters and exits through the one of the at least one toned layer and the gray glass filter;
   illuminating the calibration apparatus with light from the light source receiving, with the at least one light sensor, light scattered from the calibration apparatus; and
   comparing a signal output from the light sensor with a predetermined reference value.

\* \* \* \* \*